United States Patent
Halas et al.

(10) Patent No.: US 6,852,252 B2
(45) Date of Patent: Feb. 8, 2005

(54) USE OF METALNANOSHELLS TO IMPEDE THE PHOTO-OXIDATION OF CONJUGATED POLYMER

(75) Inventors: Nancy J. Halas, Houston, TX (US); Gregory David Hale, Houston, TX (US)

(73) Assignee: William Marsh Rice University, Houston, TX (US)

( * ) Notice: Subject to any disclaimer, the term of this patent is extended or adjusted under 35 U.S.C. 154(b) by 510 days.

(21) Appl. No.: 09/827,588

(22) Filed: Apr. 6, 2001

(65) Prior Publication Data

US 2002/0045675 A1 Apr. 18, 2002

Related U.S. Application Data

(63) Continuation-in-part of application No. 09/038,377, filed on Mar. 11, 1998, now Pat. No. 6,344,272.
(60) Provisional application No. 60/195,368, filed on Apr. 6, 2000, provisional application No. 60/040,971, filed on Mar. 12, 1997, and provisional application No. 60/040,570, filed on Mar. 14, 1997.

(51) Int. Cl.$^7$ .......................... B32B 15/02; C09K 11/06; H01B 1/04
(52) U.S. Cl. ................ 252/582; 252/503; 252/301.36; 428/403; 428/404; 428/913; 522/81
(58) Field of Search .................. 252/582, 301.36, 252/503; 428/403, 404, 903; 356/310; 522/81

(56) References Cited

U.S. PATENT DOCUMENTS

| 3,856,398 A | 12/1974 | Taylor ........................ 355/63 |
| 4,099,854 A | 7/1978 | Decker et al. .............. 350/312 |
| 4,123,396 A | 10/1978 | Rembaum et al. .......... 526/24 |
| 4,313,734 A | 2/1982 | Leuvering ................. 23/230 B |
| 4,416,998 A | 11/1983 | Adams et al. ................ 436/86 |
| 4,452,773 A | 6/1984 | Molday ...................... 424/1.1 |
| 4,481,091 A | 11/1984 | Brus et al. ............ 204/157.1 R |
| 4,624,923 A | 11/1986 | Margel ....................... 435/176 |
| 4,788,647 A | 11/1988 | McManus et al. .......... 427/123 |
| 4,979,821 A | 12/1990 | Schutt et al. ............... 356/246 |
| 5,023,139 A | * 6/1991 | Birnboim et al. ........... 428/402 |
| 5,025,147 A | 6/1991 | Durig et al. ................ 250/216 |
| 5,213,895 A | 5/1993 | Hirai et al. ................ 428/403 |
| 5,249,077 A | 9/1993 | Laronga et al. ............ 359/385 |
| 5,322,798 A | 6/1994 | Sadowski ................... 436/113 |
| 5,338,353 A | 8/1994 | Uchino et al. .............. 106/426 |
| 5,376,556 A | 12/1994 | Tarcha et al. ............... 436/525 |
| 5,451,525 A | 9/1995 | Shenkin et al. .............. 436/63 |
| 5,479,024 A | 12/1995 | Hillner et al. ........... 250/458.1 |
| 5,501,949 A | 3/1996 | Marshall ........................ 435/5 |
| 5,521,289 A | 5/1996 | Hainfeld et al. ......... 530/391.5 |
| 5,545,250 A | 8/1996 | Bergmann et al. ............ 75/252 |

(List continued on next page.)

FOREIGN PATENT DOCUMENTS

| WO | WO 90/11890 | 10/1990 | |
| WO | WO 97/40181 | 10/1997 | ........... C12N/15/87 |
| WO | WO 98/37417 | 8/1998 | ......... G01N/33/553 |

OTHER PUBLICATIONS

Hale et al , "Enhancing the active lifetime of luminescent semiconducting polymers via doping with metal nanoshells", Appl. Phys. Lett. , 2001, 78(11), pp 1502–1504.*

(List continued on next page.)

*Primary Examiner*—Mark Kopec
*Assistant Examiner*—Kallambella M. Vijayakumar
(74) *Attorney, Agent, or Firm*—Conley Rose, P.C.

(57) ABSTRACT

The present invention relates to incorporating metal nanoshells specifically designed to interact with triplet excitons in polymers. By interacting with triplet excitons, the rate of photo-oxidation can be slowed and the density of luminescence-quenching traps can be reduced.

24 Claims, 7 Drawing Sheets

U.S. PATENT DOCUMENTS

| | | | |
|---|---|---|---|
| 5,567,628 A | | 10/1996 | Tarcha et al. ............... 436/525 |
| 5,599,668 A | | 2/1997 | Stimpson et al. .............. 435/6 |
| 5,776,375 A | * | 7/1998 | Hofstraat et al. ........... 252/582 |
| 5,817,462 A | | 10/1998 | Garini et al. .................. 435/6 |
| 5,845,083 A | | 12/1998 | Hamadani et al. ..... 395/200.61 |
| 5,938,617 A | | 8/1999 | Vo-Dinh ..................... 600/476 |
| 6,180,415 B1 | | 1/2001 | Schultz et al. .............. 436/518 |
| 6,344,272 B1 | * | 2/2002 | Oldenburg et al. ......... 428/403 |
| 2003/0017264 A1 | * | 1/2003 | Treadway et al. .......... 427/212 |

OTHER PUBLICATIONS

Birnboim, Meyer H., "Nonlinear Optical Properties of Structured Nanoparticle Composites", Mat. Res. Soc. Symp. Proc. vol. 164, 1990, pp. 277–282.

Nedelijkovic, Jovan, "Observation of Plasmon–Enhanced Optical Extinction in Silver–Coated Silver Bromide Nanoparticles", American Institute of Physics, Jun. 3, 1991, pp. 2461–2463.

Oldenburg, S.J., "Nanoengineering of Optical Resonances", Chemical Physics Letters 288 (1988), pp. 243–247.

Westcott, Sarah, "Formation and Adsorption of Clusters of Gold Nanoparticle onto Functionalized Silica Nanoparticles Surfaces", Langmuir, 1998, vol. 14, No. 19, pp. 5396–5401.

Zhou, H.S., "Controlled Synthesis and Quantum–Size Effect in Gold–Coated Nanoparticles", American Physical Society, 1994, vol. 50, No. 16, pp. 12 052–12 056.

Zhou, H.S., "Synthesis and Optical Properties of Coated Nanoparticle Composites", Jornal of Luminescence, 70, 1996, pp. 21–34.

R. D. Averitt, et al; *Optical Properties and Growth Kinetics of Au coated au_2S Nanoshells*; Web Publication ; Jan. 10, 1997; (1 p.).

S. J. Oldenburg, et al; *Self–assembled Metal Shell Nanoparticles*; Web Publication; Jan. 10, 1997; (1 p.).

J. I. Steinfeld; *An Introduction to Modern Molecular Spectroscopy*; The MIT Press; Second Edition; Copyright© 1974 and 1985; (8 p.).

P. F. Bernath; *Spectra of Atoms and Molecules*; Oxford University Press 1995; (8 p.).

R. D. Averitt, et al; *Ultrafast Electron Dynamics in Gold Nanoshells*; The American Physical Society vol. 58, No. 16; 1998; (4 p.).

J. W. Haus, et al; *Nonlinear–Optical Properties of Conductive Spheroidal Particle Composites*; Optical Society of America, vol. 6, No. 4, Apr. 1989; (pp. 797–807).

D. Stroud, et al; *Decoupling Approximation for the Nonlinear–Optical Response of Composite Media*; Optical Society of America, vol. 6, No. 4, Apr. 1989; (pp. 778–786).

A. E. Neeves, et al; *Composite Structures for the Enhancement of Nonlinear–Optical Susceptibility*; Optical Society of America; vol. 6, No. 4, Apr. 1989; (pp. 787–796).

P. Barnickel, et al; *Silver Coated Latex Spheres*; Molecular Physics, 1989, vol. 67, No. 6; (pp. 1355–1372).

R. D. Averitt, et al; *Plasmon Resonance Shifts of Au–Coated $Au_2S$ Nanoshells: Insight into Multicomponent Nanoparticle Growth*; Physical Review Letters, Jun. 2, 1997, vol. 78, No. 22; (pp. 4217–4220).

D. Sarkar, et al; General Vector Basis Function Solution of Maxwell's Equations; *Physical Review , vol. 56, No. 1, Jul. 1997*; (pp. 1102–1112).

* cited by examiner

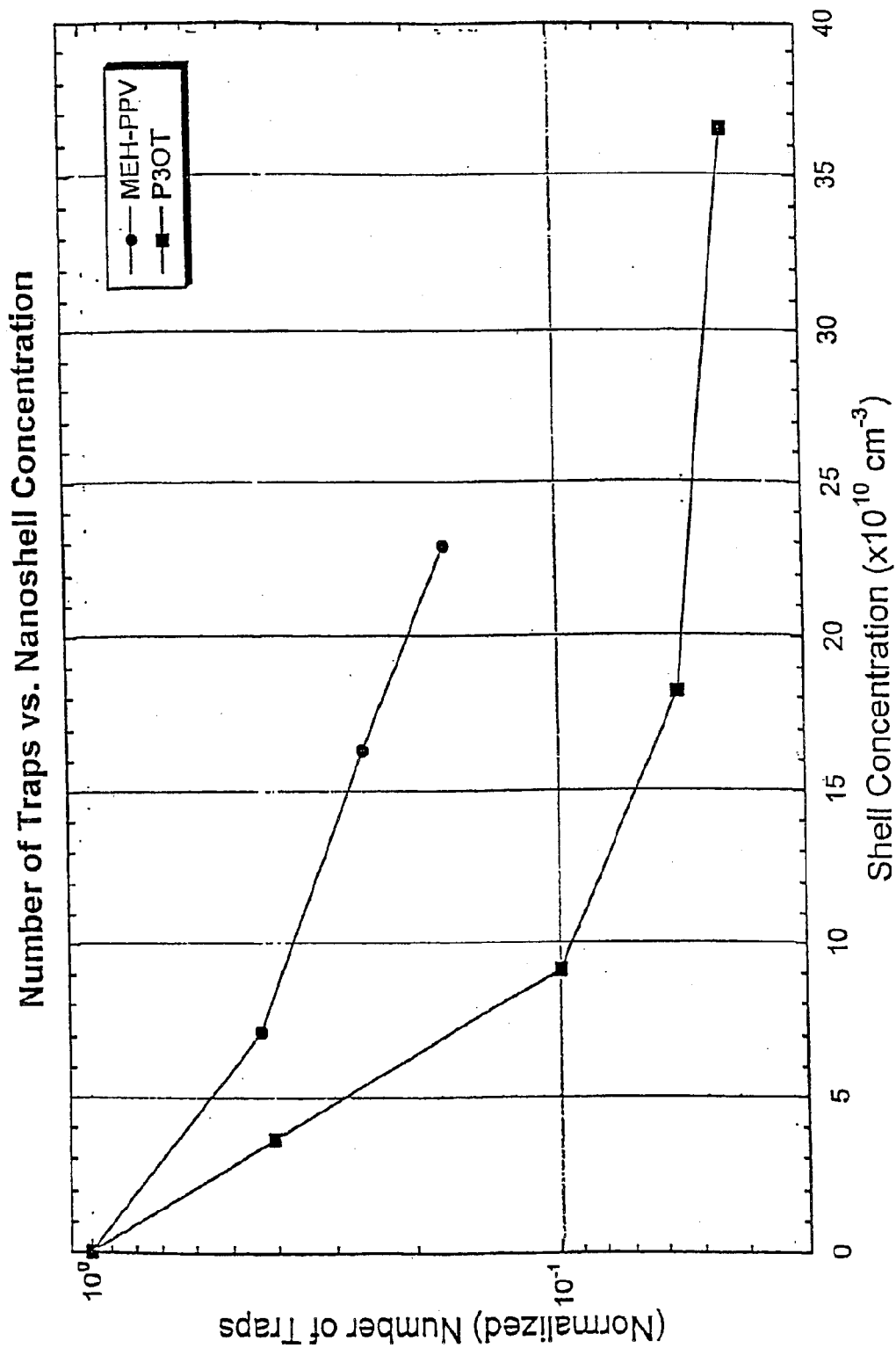

USE OF METALNANOSHELLS TO IMPEDE THE PHOTO-OXIDATION OF CONJUGATED POLYMER

CROSS-REFERENCE TO RELATED APPLICATION

The present application claims the benefit of U.S. Provisional Patent Application No. 60/195,368 filed Apr. 6, 2000 and Continuation-in-part of U.S. Utility patent application Ser. No. 09/038,377 filed Mar. 11, 1998, now U.S. Pat. No. 6,344,272 which claims the benefit of U.S. Provisional Patent Application No. 60/040,971 filed Mar. 12, 1997 and U.S. Provisional Patent Application No. 60/040,570 filed Mar. 14, 1997, the disclosures of which are incorporated herein by reference.

STATEMENT REGARDING FEDERALLY SPONSORED RESEARCH OR DEVELOPMENT

This work was partially funded by the National Science Foundation [Grant # ECS-9801707].

FIELD OF THE INVENTION

The present invention relates to a method for reducing the sensitivity of conjugated polymers to photo-oxidative degradation, thus improving the environmental stability and nominal operating lifetime of conjugated polymer-based devices.

BACKGROUND OF THE INVENTION

The use of conducting polymer thin films as the active layers in optoelectronic devices has been growing in interest for the past decade. Development of conducting polymer-based devices such as LEDs, photodiodes, flat-panel displays, solar cells, lasers, and transistors has proceeded rapidly, and in many cases commercialization is imminent. However, a major drawback to the commercialization of all these types of devices is the rapid rate of photo-oxidation of the conducting polymer under ambient conditions, which in all cases degrades device performance and ultimately limits device lifetime.

The dynamics of the photo-oxidation process in conducting polymers has been studied extensively. In photo-oxidation, a primary, nonluminescent excitation in the conjugated polymer (the triplet exciton) interacts with oxygen diffused into the polymer film, transferring energy to the oxygen and forming a highly reactive excited state of oxygen (singlet oxygen), which chemically reacts with the conjugated polymer, forming exciton traps. These exciton traps are topological defects, chemically corresponding to carbonyl defects, added on polymer chains and chain scission, which provide an additional nonradiative relaxation channel for the polymer singlet excitons, thus quenching the polymer luminescence. Hence, once sufficient exciton traps have formed, the polymer is rendered inoperable for its intended purpose.

The most widely used method for improving conducting polymer-based device lifetime is encapsulation. The range of encapsulation methods available are limited to low temperatures due to degradation of the polymer active layer at temperatures approaching the melting point (generally less than 200° C.) of the polymer. Typical encapsulation methods for polymer-based devices include deposition of multiple organic or inorganic layers, which may be doped with oxygen scavengers, sandwiching the device between glass substrates bonded with epoxy, or a combination of the two. Devices using a combination of these techniques have demonstrated to have operating lifetimes in excess of 10,000 hours and storage lifetimes of at least 2 years, determined by accelerating testing conditions (elevated temperature and humidity). However, these techniques are limited to devices on rigid substrates. One possible advantage of conducting polymer-based devices over inorganic devices is the ability to fabricate devices on flexible substrates, allowing for simple mass production by reel-to-reel coating. To the inventors' knowledge, this advantage cannot readily be realized, because encapsulated flexible polymer devices are not yet commercially available.

Another method of protecting conducting polymer films against photo-oxidation is the addition of a stabilizer material to block the action of the oxygen. Several materials generally used to combat oxidation in polymers such as polyethylene have been studied in polythiophene devices, with no observable effect. For example, significant protection against photo-oxidation was afforded to polythiophene derivatives by the addition of 1-phenyldodecan-1-one (PDK). However, the additive (PDK) was shown to protect the polymer by absorbing UV light without transferring energy to the polymer. This protection is of no use in electroluminescent devices, which operate on the principle of electron-hole recombination, instead of photon absorption to form radiative species. Electron-hole recombination utilizes energy applied to electron-hole junctions to excite atoms and subsequently maintain light emission. Alternatively, the addition of $C_{60}$ to polyphenylenevinylene derivatives has been shown to drastically reduce photo-oxidation of the polymer. Unfortunately, the $C_{60}$ has the additional undesirable effect of efficiently quenching the luminescence of the polymer.

Because the desire to produce conducting polymer-based devices continues to grow, there exists a need to develop a method that improves the properties of the polymers used, namely by reducing photo-oxidation in the polymers without adversely affecting other properties of the polymers.

SUMMARY OF THE INVENTION

The present invention utilizes specially designed nanoparticles known as metal nanoshells to impede the photo-oxidation process in optoelectronic devices. Metal nanoshells are composite nanoparticles consisting of a dielectric core coated by a thin metal shell, which exhibit a geometrically tunable plasmon resonance, which in turn allows tailoring of the optical properties (light absorption and scattering) by varying the ratio of the core radius to the shell thickness.

By adding metal nanoshells designed to interact specifically with the conjugated polymer triplet excitons and providing a relaxation pathway for the triplet excitons, a competing process to photo-oxidation is introduced. A significant reduction in the degradation of the luminescent optical properties of the conjugated polymer/metal nanoshell composite films relative to the pristine conjugated polymer films is observed with no concomitant negative effects on the luminescent characteristics themselves. The photo-oxidation induced defect density in the conjugated polymer is reduced by as much as a factor of twenty by adding metal nanoshells.

It will be understood that the term "pristine" is intended to differentiate polymer/metal nanoshell composite films from polymer films that are essentially nanoshell-free. This is not to say that the essentially nanoshell-free polymer films do not contain impurities.

The present invention is applicable to optoelectronic devices that rely upon the luminescent properties of conjugated polymers, and more generally to any molecular systems that are prone to photo-oxidation.

In accordance with a preferred embodiment of the present invention, a method for reducing photo-oxidation in a molecular system includes incorporating into the molecular system metal nanoshells that possess a plasmon resonance approximately equal to a desired wavelength.

In accordance with another preferred embodiment of the present invention, a method for improving the stability and lifetime of a polymer system includes incorporating metal nanoshells into the polymer system that possess a plasmon resonance approximately equal to a desired wavelength.

Alternately, in accordance with a preferred embodiment of the present invention, a method for providing a relaxation pathway for triplet excitons includes metal nanoshells having a plasmon resonance corresponding to the triplet exciton-ground state transition energy.

In accordance with another preferred embodiment of the present invention, a method for providing a competing process for singlet oxygen formation includes metal nanoshells having a plasmon resonance approximately equal to a desired wavelength.

In accordance with yet another preferred embodiment of the present invention, a photoconductive polymer system includes metal nanoshells incorporated into a photoconductive polymer, where the metal nanoshells have a plasmon resonance frequency tailored to the polymer system. Also according to the present invention, metal nanoshells can be incorporated into other polymeric and non-polymeric systems that are subject to photo-oxidation for the purpose of mitigating such photo-oxidation.

In accordance with still yet another preferred embodiment of the present invention, a method for incorporating metal nanoshells into a molecular system includes preparing a metal nanoshell solution using appropriate solvents, preparing a molecular system solution using appropriate solvents, and adding predetermined amounts of the metal nanoshell solution to the molecular system solution to reach a desired metal nanoshell concentration.

BRIEF DESCRIPTION OF THE DRAWINGS

A better understanding of the present invention can be obtained when the following detailed description of a preferred embodiment is considered in conjunction with the following drawings:

FIG. 7 is a graph showing number of traps vs. nanoshell concentration.

DETAILED DESCRIPTION OF THE INVENTION

Figure 1:
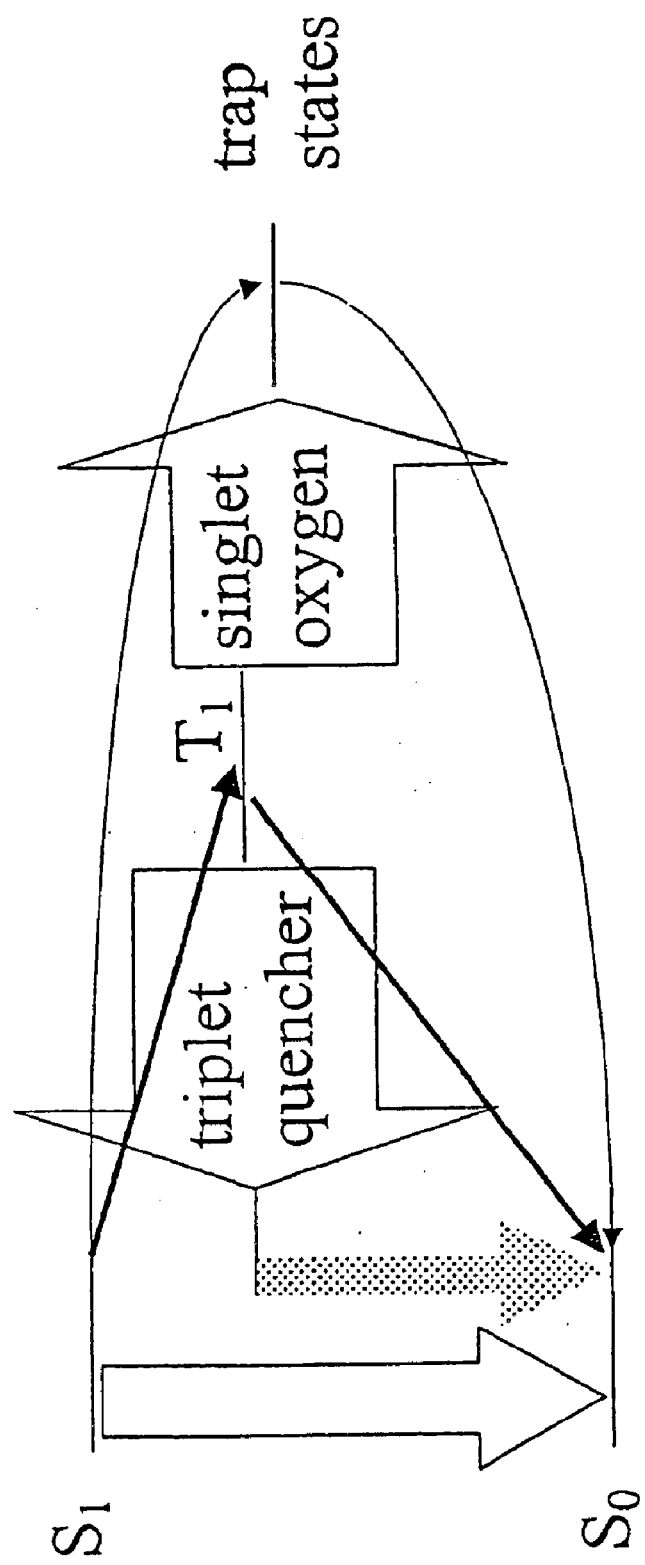
FIG. 1 is a diagram showing the general overview of a preferred embodiment of the present invention.

The present invention relates to adding metal nanoshells to conducting polymers or other molecular systems that are vulnerable to photo-oxidation. As shown in FIG. 1, in one embodiment, a triplet quencher (metal nanoshells) is added to a polymer film. The metal nanoshells preferentially interact with the polymer triplet exciton, forming a relaxation pathway. By providing an additional de-excitation channel for the triplet exciton, it is possible to compete with singlet oxygen formation. Due to the central role of polymer triplet exciton $T_1$ in the photo-oxidation process, control over the triplet exciton dynamics leads to control over the photo-oxidation process. By providing an additional de-excitation channel for the triplet exciton, the rate of singlet oxygen formation and resultant photo-oxidation of the polymer can be reduced.

In order for the nanoshells to interact with the polymer triplet exciton, the metal nanoshells are fabricated such that their plasmon resonance overlaps the conjugated polymer triplet exciton-ground state transition energy. In a preferred embodiment, the metal nanoshells are fabricated such that their plasmon resonance wavelength corresponds to a wavelength for which the photon energy is equal to approximately 0.75–1.25 times, and more preferably 0.95 to 1.05 times, the conjugated polymer triplet exciton-ground state transition energy. Nanoshells that are fabricated with a pre-selected plasmon resonance are sometimes referred to herein as "tuned" nanoshells.

A preferred fabrication process for metal nanoshells consists of four steps. First, the Stöber method is used to grow monodisperse silica cores. Second, the silica cores are coated with an aminosilane layer. Next, the core surface is decorated with small colloidal gold particles. Finally, the small gold particles are used as reduction sites for the deposition of gold. For a more detailed description, see U.S. Utility patent application Ser. No. 09/038,377.

Metal nanoshells suitable for use in the present invention include complete shells, hollow shells, partial shells (cups), and, in particular gold-gold sulfide shells. Additionally, it is contemplated that a reduction in photo-oxidation can be achieved in accordance with the present invention by including the "tuned" nanoshells in proximity to the photo-oxidizable structure, i.e. without actually mixing the nanoshells into the photo-oxidizable molecular system.

The Stöber method is a base-catalyzed reaction of tetraethylorthosilicate and can produce monodisperse spherical silica particles. The particle size is controlled by the relative reactant concentrations and typically falls in the range of 80 to 1000 nm, with a dispersity of <15%.

The silica nanoparticles produced in this manner are coated with 3-aminopropyltrimethoxysilane (APTMS). Enough APTMS to coat the surface of the silica nanoparticles with several monolayers is added and the mixture is boiled to promote condensation of the silane groups with the silica surface. This results in the termination of the silica nanoparticle surfaces with amine groups.

Ultrasmall gold colloid is fabricated according to the method described by D. G. Duff et al. in "A New Hydrosol of Gold Clusters .1. Formation and Particle-Size Variation," Langmuir 9,2301 (1993) and concentrated using rotary evaporation. The functionalized silica nanoparticles are added to the concentrated gold colloid in a quantity calculated to result in approximately 30% gold colloid coverage on the silica nanoparticle surface. The gold colloid covalently bonds to the amine-terminated nanoparticle surface.

The gold shell is grown by adding the gold colloid-decorated silica nanoparticles to a chloroauric acid/potassium carbonate solution with a reducing agent (either sodium borohydride or formaldehyde). The gold in solution is reduced onto the attached gold colloid, which grows into gold islands and eventually coalesces into a complete shell. The thickness of the shell is determined by the relative amounts of reactants in this final step. By "sweeping" through several variations in reactive amounts, the necessary parameters to optimize the metal nanoshell fabrication process are determined. Typical nanoshell thicknesses grown by this method are 8 to 20 nm.

Once the metal nanoshells are produced, they are then concentrated and transferred to an organic solvent that is compatible with conjugated polymer solution processing. Next, solutions of the conjugated polymer are prepared using appropriate solvents (i.e. chloroform or chlorobenzene). Small amounts of the metal nanoshell solution are added to the conjugated polymer solution to reach the desired metal nanoshell concentration. The resulting conjugated polymer/metal nanoshell solution can then be used in standard device processing steps such as spin coating, drawing, extrusion, evaporative deposition, molding and the like. In one embodiment, it is preferred that the metal nanoshells comprise between 10 and 50 percent of the volume fraction of the overall molecular system.

Because the typical conjugated polymer film thicknesses used in devices such as LEDs (100–200 nm) is similar to the diameter of some nanoshells, the use of nanoshells in LEDs and other thin film applications will likely require the selection of smaller diameter nanoshells. Additionally, because alternative LED fabrication techniques are currently being developed to improve device efficiency, such as employing additional, somewhat thicker, organic layers around the active conjugated polymer layer, next generation devices may not suffer from metal nanoshell size limitations. For example, it may be possible to disperse metal nanoshells into a thicker secondary layer in these LEDs. As will be noted, other conjugated polymer-based device structures such as conjugated polymer-based lasers use significantly thicker active regions and thus should be less sensitive to the size of the metal nanoshells.

A possible variation of the present invention is in the field of "small organic molecule"-based electroluminescent devices such as hydroxy quinoline aluminum (AlQ3) devices, or organic light emitting devices (OLEDs). This technology has developed parallel to, and in many ways in competition with, conjugated polymer technology. It consists of using luminescent organic molecules as the active layer in optoelectronic devices. The organic molecules employed in these devices suffer a similar propensity to photo-oxidative degradation.

It should be understood that the present invention does not turn the photo-oxidation process off, rather it impedes its progress. Encapsulation techniques are currently being employed in conjugated polymer device fabrication that greatly reduce the rate of photo-oxidation by keeping oxygen out of the device. The addition of metal nanoshells to conjugated polymer devices should be an excellent complement to encapsulation, yielding even longer device lifetimes.

When metal shell nanoparticles with resonances tuned to the polymer's triplet exciton energy are added to the conducting polymer, the resultant nanoparticle-polymer composite exhibits dramatically reduced photo-oxidation rates with essentially no change in the luminescent properties, materials properties, or processing characteristics of the conducting polymer. While the example below uses gold nanoshells, other metals could be used besides gold, including coinage metals, noble metals, transition metals, and synthetic metals such as polyacetylene and polyanaline.

EXAMPLE

Gold nanoshells (silica core-gold shell nanoparticles) exhibit a strong optical resonance (plasmon resonance) whose frequency is sensitively dependent on the ratio of the nanoparticle's core and shell dimensions. Changing this ratio allows the nanoshell resonance to be placed at any wavelength of choice across a broad spectral region spanning the visible to the mid-infrared. In this set of experiments, gold nanoshells were designed such that their plasmon frequency was resonant with the triplet exciton-ground state energy transition in two different conducting polymers, poly[2-methoxy-5-(2'-ethylhexyloxy)-1,4-phenylenevinylene] (MEH-PPV) and poly(3-octylthiophene) (P3OT). The nanoshells were dispersed in polymer solutions (MEH-PPV/chlorobenzene and P3OT/chloroform), that were then spin-cast onto glass substrates to create nanoshell-containing films. Control films including the same polymers without nanoshells were also formed. No visible difference between the pristine polymer films and the polymer-nanoshell composite films was observed. The substrates were held under vacuum and photoluminescence [was excited using 488 nm light and collected using a monochromator and a photomultiplier tube. At the concentrations used, the absorbance of the nanoshells at the excitation wavelength was negligible. The sample chamber was then opened to ambient air and the decay of the photoluminescence was monitored at the luminescence maximum over the timescale of several minutes.

Figure 2:
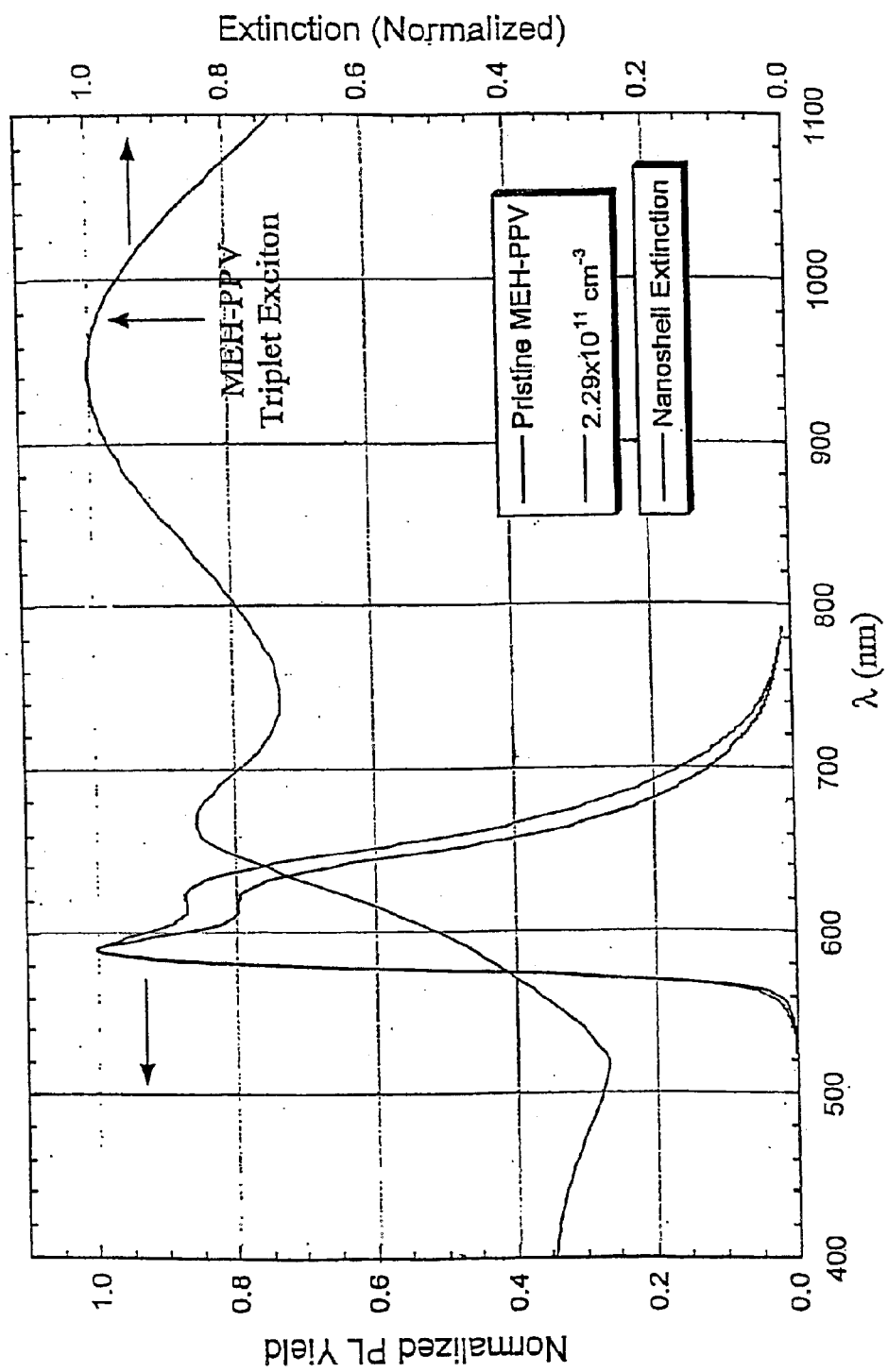
FIGS. 2 and 3 are graphs showing representative photoluminescence spectra.
Figure 3:
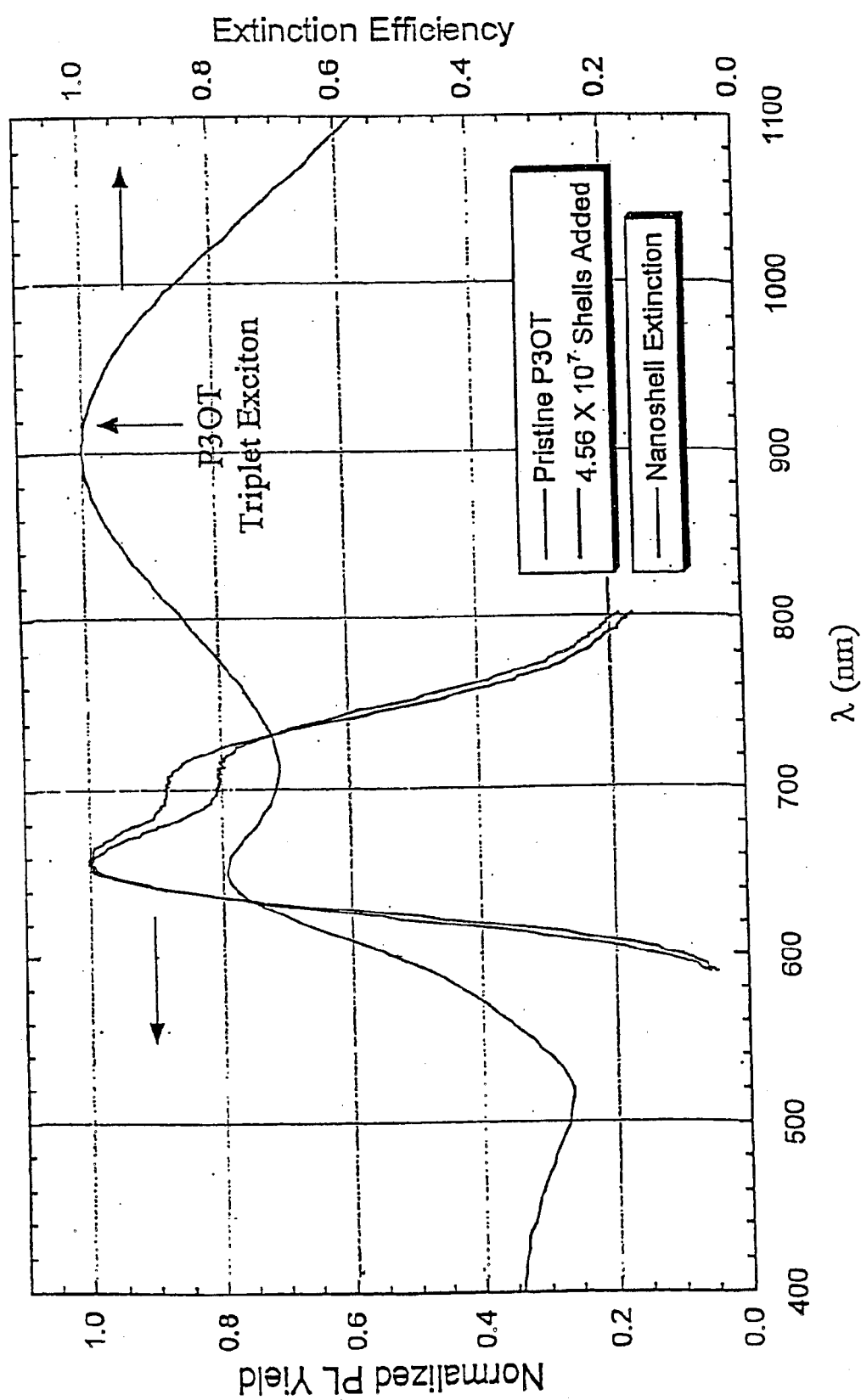

A representative photoluminescence (PL) spectrum for each respective pristine polymer 20 and polymer-nanoshell composite 30 is shown in FIGS. 2 and 3. In both cases, the relative quantum yield of the pristine polymer was not changed by the addition of nanoshells to the polymer. The nanoshell extinction 10 is also shown. The relative heights of the two features observed in each polymer PL spectrum vary slightly between samples, as well as on each sample, but show no dependence on nanoshell concentration, indicating that these deviations are most likely due to variations in the local structure of the polymer and polymer-nanoshell composite films.

Figure 4:
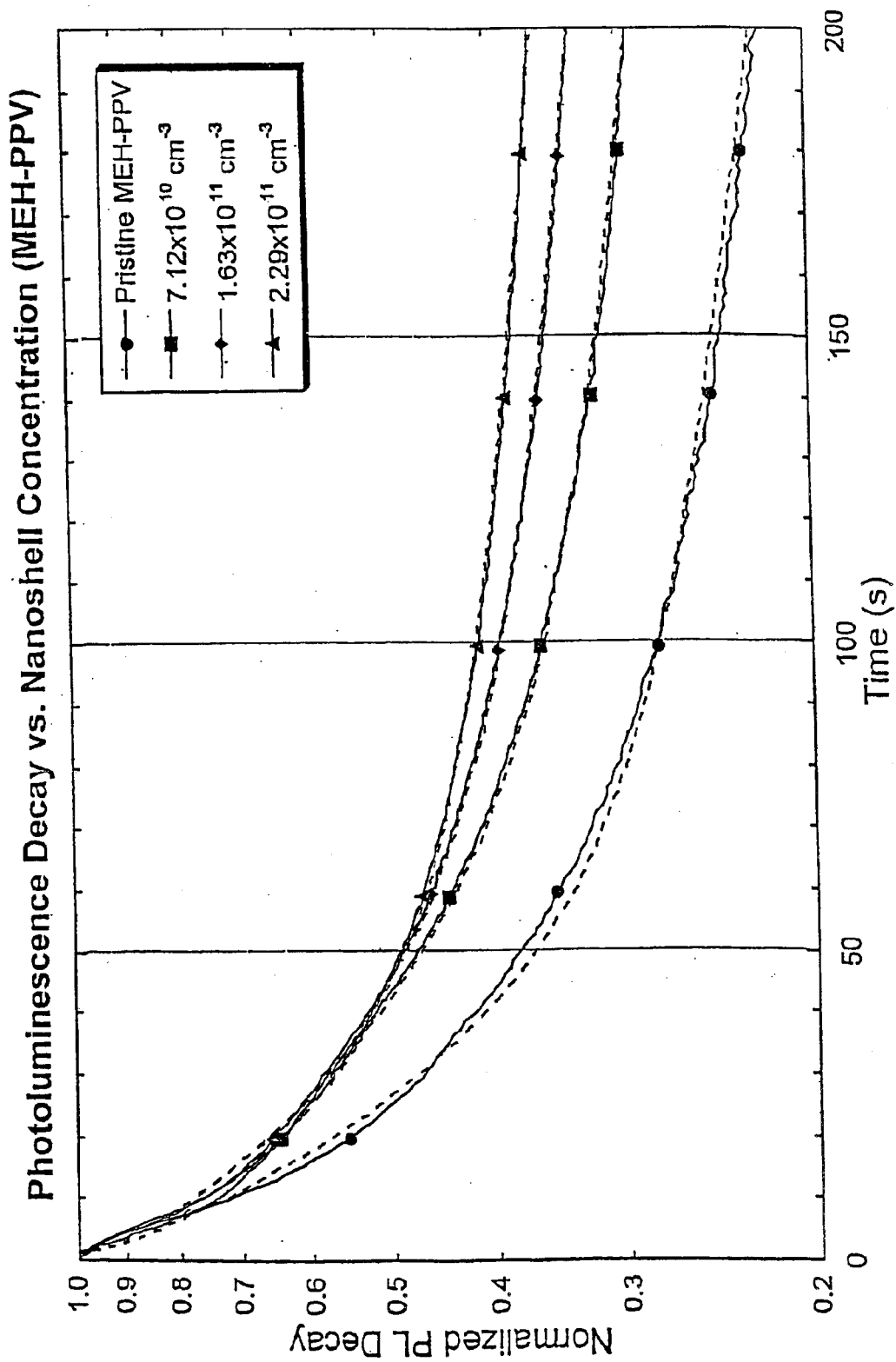
FIGS. 4 and 5 are graphs showing photoluminescence decay vs. nanoshell concentration.
Figure 5:
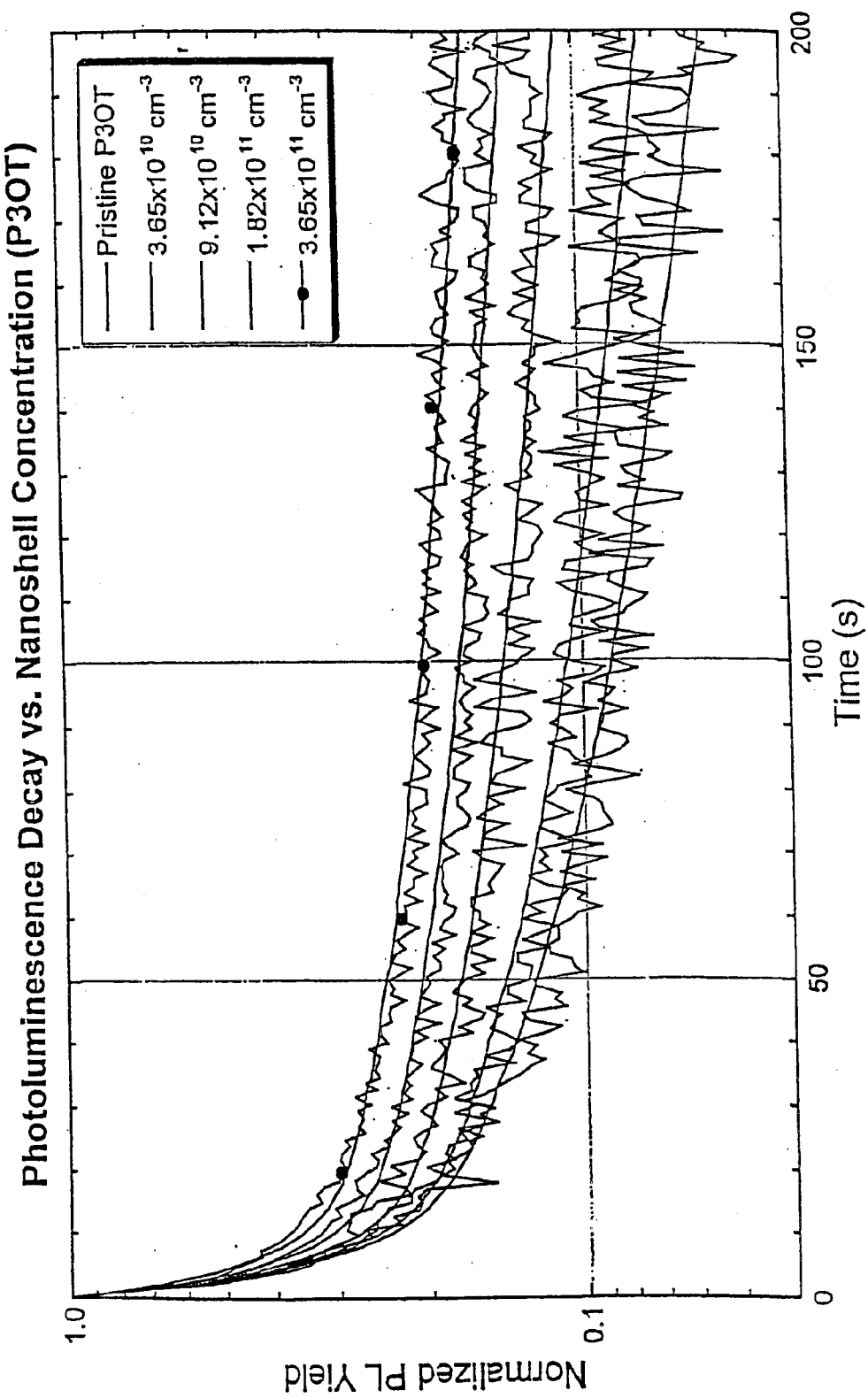

The photoluminescence decay for polymer-nanoshell composite films having a range of nanoshell concentrations is shown in FIGS. 4 and 5. In both cases, the addition of nanoshells to the polymer corresponds to a dramatic decrease in the decay of the photoluminescence signal upon exposure to ambient temperature. The time-dependent response of the photoluminescence quenching is believed to be a combination of a fast, reversible component followed by a slower, nonreversible component with dynamics consistent with exciton trap formation on a 1D lattice:

$$\Phi_{PL} = A\exp\left[-\left(\frac{t}{\tau_{fast}}\right)\right] + B\exp\left[-\left(\frac{t}{\tau_{trap}}\right)^{\frac{1}{3}}\right] \quad (1)$$

where $\tau_{trap}=[2\tau^2(3/2)^3 D_{diff} n_{1D}^2]^{-1}$ depends on the rate of oxygen diffusion into the polymer film and $(n_{1D})$ is the one-dimensional density of exciton traps on a polymer chain.

Figure 6:
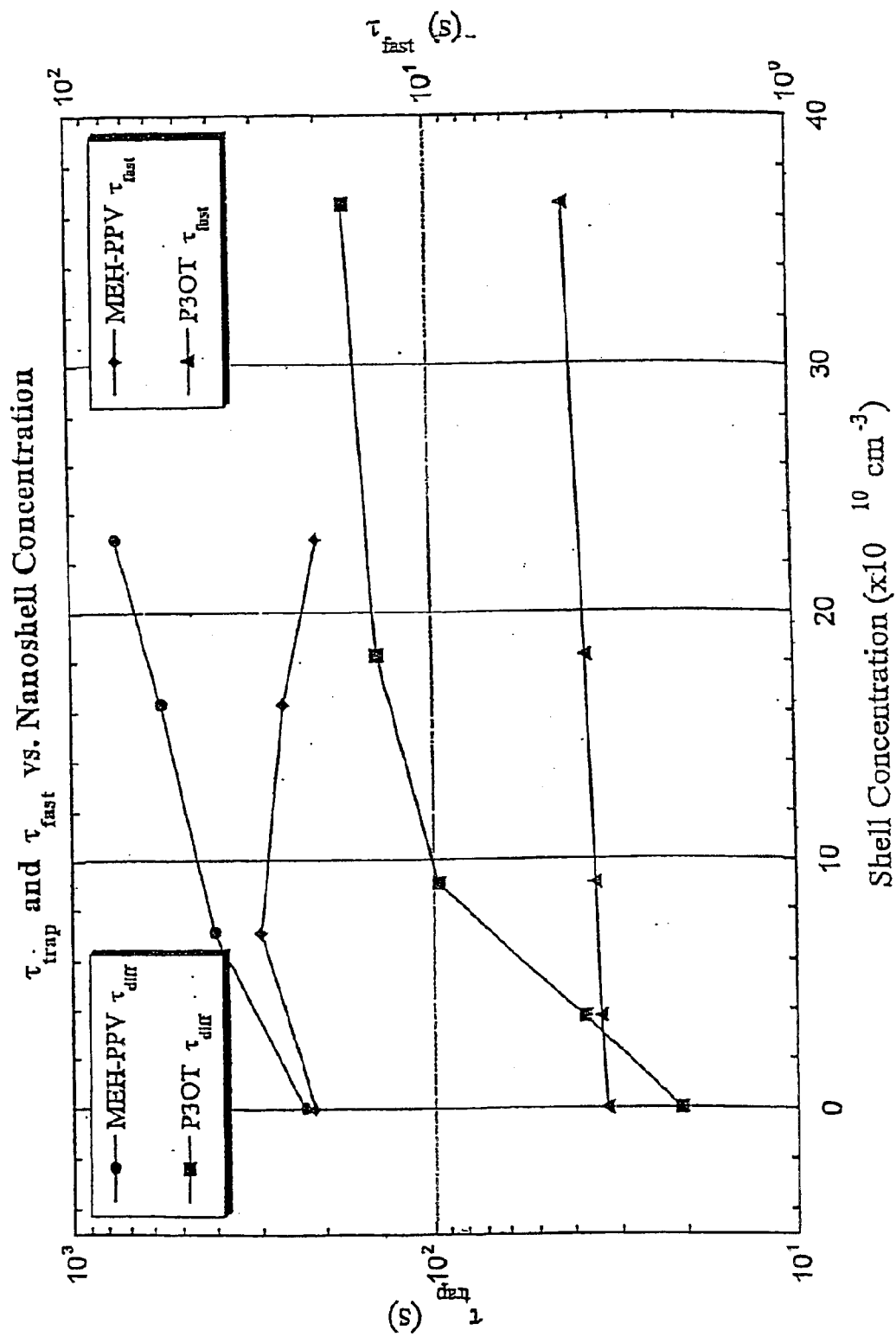
FIG. 6 is a graph showing time-dependent response of photoluminescence quenching vs. nanoshell concentration.

The lifetimes, $\tau_{trap}$ and $\tau_{fast}$, of Equation 1 for the various nanoshell concentrations used are shown in FIG. 6. The fast lifetime is significantly shorter in P3OT (3–4 s) than MEH-PPV (20–30 s), but is insensitive to the nanoshell concentration in either case. The shorter lifetime in P3OT may be indicative of a reversible polymer-oxygen charge transfer (CT) complex forming in the P3OT film that leads to the observed luminescence quenching.

The trap formation lifetime ($\tau_{trap}$) values determined from the data shown in FIG. 4 show similar behavior for both P3OT-based and MEH-PPV-based films. The increase in $\tau_{trap}$ indicates that the rate of trap formation decreases as the nanoshell concentration is increased.

It has been previously shown that the volume density of photo-oxidation induced defects is related to the trap formation lifetime: $n_T \sim (\tau_{trap})^{-3/2}$. Values for n, normalized to the defect density for the pristine polymer films, are shown in FIG. 7 as a function of nanoshell concentration. Again, the defect density in P3OT has stronger concentration dependence than in MEH-PPV. The defect density in P3OT is reduced by more than a factor of 20, while that in MEH-PPV is reduced by more than a factor of five.

While not wishing to be bound by any particular theory, the inventors believe that the metal nanoshells may inhibit photo-oxidation in the composites by directly de-exciting singlet oxygen. The luminescence quenching rate in polymer-nanoshell composites with a nanoshell plasmon resonance energetically overlapping both the triplet exciton and singlet oxygen (1270 nm) is the same as the quenching rate observed when the plasmon is resonant with the triplet exciton but not with singlet oxygen. Thus it is inferred that nanoshell resonant de-excitation of triplet excitons is a plausible mechanism for this effect.

It has been shown that adding metal nanoshells to conjugated polymer films decreases the susceptibility of the polymer to photo-oxidative degradation by providing a triplet exciton decay pathway that competes with singlet oxygen formation. In P3OT, a concentration of 0.1% by volume of nanoshells shows a saturation of this effect, reducing the number of luminescence-quenching exciton traps by a factor of 20. These results indicate that polymer-nanoshell composites may prove useful in the development of robust, practical polymer devices for a range of commercializable applications including, but not limited to photodetectors, solar cells, LEDs, semiconductor lasers, optical fibers, Erbium-doped fiber amplifiers and liquid-crystal displays including dynamic scattering mode displays, twisted nematic displays, thin-film transistor displays, and supertwist nematic displays.

The present invention is applicable to any molecular system that is vulnerable to this type of decay, namely photo-oxidation. These include but are not limited to conductive, photo-conductive, semi-conductive, conjugated, and photoluminescence polymers, and other organic molecular systems. Further, nanoshells that are suitable for use in the present invention include gold/gold sulfide, hollow shells, partial shells (known as "cups"). It is further believed that the advantages of the present invention can be realized by including nanoshells in a layer that is separate and adjacent to a polymer.

While the preferred embodiments of the invention have been shown and described, modifications thereof can be made by one skilled in the art without departing from the spirit and teachings of the invention. For example, although a preferred use of a triplet quencher (metal nanoshells) is for impeding photo-oxidation in conducting luminescent polymer systems, one can readily appreciate that similar triplet quenchers could find use in a variety of industrial applications where electron-hole junctions are depleted, and utilize energy to excite electrons. Furthermore, the embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims. The disclosures of "Impeded Photo-Oxidation of Conducting Polymer Films Using Metal Nanoshells" by Gregory Hale (2000 Electrical Engineering Thesis, Rice University) and all patents and publications cited herein are incorporated by reference.

What is claimed is:

1. A method for reducing photo-oxidation in a molecular system that is vulnerable to photo-oxidation, comprising: providing metal nanoshells having a plasmon resonance approximately equal to a desired wavelength in sufficient proximity to the molecular system to prevent oxidation.

2. The method of claim 1 wherein said metal nanoshells are incorporated into the molecular system.

3. The method of claim 1 wherein said molecular system comprises a polymer.

4. The method of claim 3 wherein said polymer comprises a photoconductive polymer.

5. The method of claim 4 wherein said photo-conductive polymer comprises a flexible polymer.

6. The method of claim 1 wherein the metal in said metal nanoshells is selected from the group consisting of coinage metals, noble metals, transition metals, and synthetic metals.

7. The method of claim 5 wherein said metal nanoshells comprise gold.

8. The method of claim 7 wherein said metal nanoshells comprise between 10 and 50 percent of the volume fraction of the overall molecular system.

9. The method of claim 1 wherein said desired wavelength is between 650 and 2500 nm.

10. The method of claim 1 wherein said desired wavelength is between 650 and 1000 nm.

11. The method of claim 1 wherein said desired wavelength has a photon energy that is equal to between about 0.75 and about 1.25 times the exciton-ground state transition energy.

12. A method for improving the stability and lifetime of a polymer system comprising incorporating metal nanoshells into said polymer system, wherein said metal nanoshells have a plasmon resonance approximately equal to a desired wavelength.

13. A method for providing a relaxation pathway for triplet excitons having a exciton-ground state transition energy, comprising absorbing the exciton-ground state transition energy with metal nanoshells having a plasmon resonance corresponding to the triplet exciton-ground state transition energy.

14. The pathway of claim 13 wherein said metal nanoshells impede singlet oxygen formation.

15. The pathway of claim 14 wherein impeded singlet oxygen formation results in reduced photo-oxidation in a molecular system.

16. A method for providing a competing process for singlet oxygen formation in a molecular system, comprising including in the system metal nanoshells having a plasmon resonance approximately equal to a desired wavelength.

17. The process of claim 16 wherein reduced singlet oxygen formation results in reduced photo-oxidation of the molecular system.

18. The method of claim 16 wherein said desired wavelength has a photon energy that is equal to between about 0.75 and about 1.25 times the transition energy for singlet oxygen formation.

19. The process of claim 16 wherein said desired wavelength is between 650 and 2500 nm.

20. A photoconductive polymer system comprising metal nanoshells incorporated into a photo-conductive polymer, wherein said metal nanoshells have a plasmon resonance tuned to an energy state of said polymer system.

21. The polymer system of claim 20 wherein the photo-conductive polymer is photo-luminescent.

22. A method for incorporating metal nanoshells into a molecular system comprising:
- preparing a metal nanoshell solution;
- preparing a molecular system precursor; and
- adding predetermined amounts of the metal nanoshell solution to the molecular system precursor to reach a desired metal nanoshell concentration.

23. The method of claim 22 wherein said metal nanoshell solution is prepared by providing metal nanoshells in an organic solvent, wherein said organic solvent is compatible with the molecular system precursor.

24. The method of claim 22 further comprising:
- processing the resulting molecular system precursor/metal nanoshell solution so as to form a photo-oxidation protected molecular system.

* * * * *

UNITED STATES PATENT AND TRADEMARK OFFICE
CERTIFICATE OF CORRECTION

| | | |
|---|---|---|
| PATENT NO. | : 6,852,252 B2 | Page 1 of 1 |
| APPLICATION NO. | : 09/827588 | |
| DATED | : February 8, 2005 | |
| INVENTOR(S) | : Nancy J. Halas et al. | |

It is certified that error appears in the above-identified patent and that said Letters Patent is hereby corrected as shown below:

In column 1, lines 20-21, replace "This work was partially funded by the National Science Foundation [Grant # ECS-9801707]." with --This invention was made with government support under Grant Number ECS-9801707 awarded by the National Science Foundation (NSF). The government has certain rights in the invention.--

Signed and Sealed this
Ninth Day of August, 2011

David J. Kappos
*Director of the United States Patent and Trademark Office*